(12) United States Patent
Fischer et al.

(10) Patent No.: US 11,998,667 B2
(45) Date of Patent: Jun. 4, 2024

(54) AIR PURIFICATION DEVICE

(71) Applicant: Energy Harness Corporation, Cape Coral, FL (US)

(72) Inventors: Michael J. Fischer, Babcock Ranch, FL (US); Peter J. Lehrer, Sarasota, FL (US)

(73) Assignee: Energy Harness Corporation, Cape Coral, FL (US)

( * ) Notice: Subject to any disclaimer, the term of this patent is extended or adjusted under 35 U.S.C. 154(b) by 108 days.

(21) Appl. No.: 17/375,771

(22) Filed: Jul. 14, 2021

(65) Prior Publication Data
US 2022/0016299 A1    Jan. 20, 2022

Related U.S. Application Data

(60) Provisional application No. 63/051,536, filed on Jul. 14, 2020.

(51) Int. Cl.
*A61L 9/20* (2006.01)
*G01P 3/00* (2006.01)

(52) U.S. Cl.
CPC ............... *A61L 9/20* (2013.01); *G01P 3/00* (2013.01); *A61L 2202/11* (2013.01); *A61L 2202/14* (2013.01)

(58) Field of Classification Search
None
See application file for complete search history.

(56) References Cited

U.S. PATENT DOCUMENTS

| | | |
|---|---|---|
| 5,612,001 A | 3/1997 | Matschke |
| 7,234,844 B2 | 6/2007 | Bolta et al. |
| 7,690,802 B2 | 4/2010 | Higley et al. |
| 8,350,228 B2 | 1/2013 | Walker |
| 8,859,994 B2 | 10/2014 | Deal |
| 9,289,527 B1 | 3/2016 | Lichtblau |
| 9,457,120 B2 | 10/2016 | Matsui |
| 9,517,280 B2 | 12/2016 | Lynn, II et al. |
| 9,737,842 B2 | 8/2017 | Matlin et al. |
| 9,993,571 B2 | 6/2018 | Lin et al. |
| 10,143,064 B2 | 11/2018 | Zimmerman et al. |
| 10,293,066 B2 | 5/2019 | Payton |
| 2002/0031460 A1 | 3/2002 | Kulp |
| 2003/0155228 A1 | 8/2003 | Mills |
| 2006/0207431 A1* | 9/2006 | Baca ................ A61L 2/24 96/224 |
| 2009/0004046 A1 | 1/2009 | McEllen |
| 2010/0044319 A1 | 2/2010 | Engel et al. |

(Continued)

FOREIGN PATENT DOCUMENTS

| | | | |
|---|---|---|---|
| EP | 3568165 A1 | 11/2019 | |
| RU | 2600792 C1 * | 10/2016 | ............ A61L 9/14 |
| WO | WO2018101943 A1 | 6/2018 | |

*Primary Examiner* — Andrew Smyth
(74) *Attorney, Agent, or Firm* — Patrick Stanzione; Stanzione & Associates, PLLC

(57) ABSTRACT

A multichannel air purification device comprising a plurality of adjacent air channels in fluid communication with one another having a UV-C light source illuminate at least one air flow chamber, an air input means for allowing air into the channels, an air output means for allowing the air to exit the channels, openings between the channels for allowing air to pass from one channel to another channel, and a fan for drawing air through the device.

5 Claims, 6 Drawing Sheets

(56) References Cited

U.S. PATENT DOCUMENTS

2018/0021471 A1* 1/2018 Krosney .............. B01D 53/007
    422/4
2021/0317981 A1* 10/2021 Higgins ................... F21V 3/00

* cited by examiner

AIR PURIFICATION DEVICE

BACKGROUND OF THE INVENTION

The present invention is directed to an air purification device. More particularly, it is directed to an air purification device that can be placed into or on existing ceilings and operated while an area is inhabited.

It is known that deep ultraviolet light having wavelengths of 200-350 nm adversely affects the reproductive ability of microorganisms at a nucleic level. Ultraviolet light damages the very nucleotides responsible for the formation of DNA and RNA; Adenine, Cytosine, Guanine, Thymine (in DNA). Adenine, Cytosine, Guanine, Uracil (in RNA).

Air purification devices, called sterilization lamps, mostly using low-pressure mercury bulbs, have been widely used in many applications. Some of these devices employ mechanical air movement systems that draw in air, circulate it through an internal chamber, expose it to ultraviolet light and exhaust the treated air back into the surrounding area. These lamps produce much of their light at the 253.7 nm wavelength, but also produce ultraviolet light across the entire UV spectrum, with measurable amounts below 240 nm, which is known to produce harmful levels of ozone when released into the air surrounding the apparatus.

It is also known that if directly exposed to human tissue, ultraviolet light has harmful effects, such as erythema (reddening of the skin) and conjunctivitis (inflammation of the mucous membranes of the eye). Therefore, many of these fixtures cannot be safely operated when humans are present. However, design measures can be taken to prevent leakage of the ultraviolet rays from the fixtures while in operation to eliminate these adverse effects on humans.

It is also widely known that the effectiveness of ultraviolet light on the process of sterilization is determined by four distinct factors: (1) frequency, the ultraviolet light source wavelength (measured in nanometers), and how close to the maximum germicidal effective nanometer range of 265 nm-270 nm; (2) intensity, the ultraviolet light source intensity measured in $mw/cm^2$; (3) proximity, the relative distance of the ultraviolet light source to the micro-organism; (4) duration, the length of time the micro-organism is exposed to the ultraviolet wavelength; all of which work together to create the exposure dosage $mJ/cm^2$ (measured in microjoules per square centimeter), the relative strength or irradiance of the ultraviolet rays. It is further known that by maximizing these four factors, a rate of 99.9% (or higher) purification is possible.

It has been shown that many pathogens are airborne. It has also been shown that ultraviolet light has an adverse effect on the reproductive ability of pathogens and that air has an exceptionally high transmissive rate of ultraviolet light. Present air purification systems cannot control all four of the major factors of ultraviolet light (wavelength, intensity, proximity, and duration) in the air sterilization process in order to maximize their effectiveness. The present invention aims to achieve this. It controls the wavelength with precise solid state LED technology, the intensity is controlled with LED chips strategically placed on circuit boards and controllable constant current power supply, the proximity control is based on alternating or parallel or serial chamber spaces which are height and width constrained, and the duration is controlled by airflow speed based on fan control settings as well as the total quantity and total distance of alternating or serial or parallel chambers in a fixture.

SUMMARY OF THE INVENTION

The invention relates to a multichannel air purification device comprising a plurality of adjacent air channels in fluid communication with one another having a UV-C light source illuminate at least one air flow chamber, an air input means for allowing air into the channels, an air output means for allowing the air to exit the channels, openings between the channels for allowing air to pass from one channel to another channel, and a fan for drawing air through the device.

BRIEF DESCRIPTION OF THE DRAWINGS

The foregoing and other features and advantages of the present invention will become apparent to those skilled in the art to which the present invention relates upon reading the following description with reference to the accompanying drawings, in which.

DETAILED DESCRIPTION OF THE INVENTION

Figure 1:
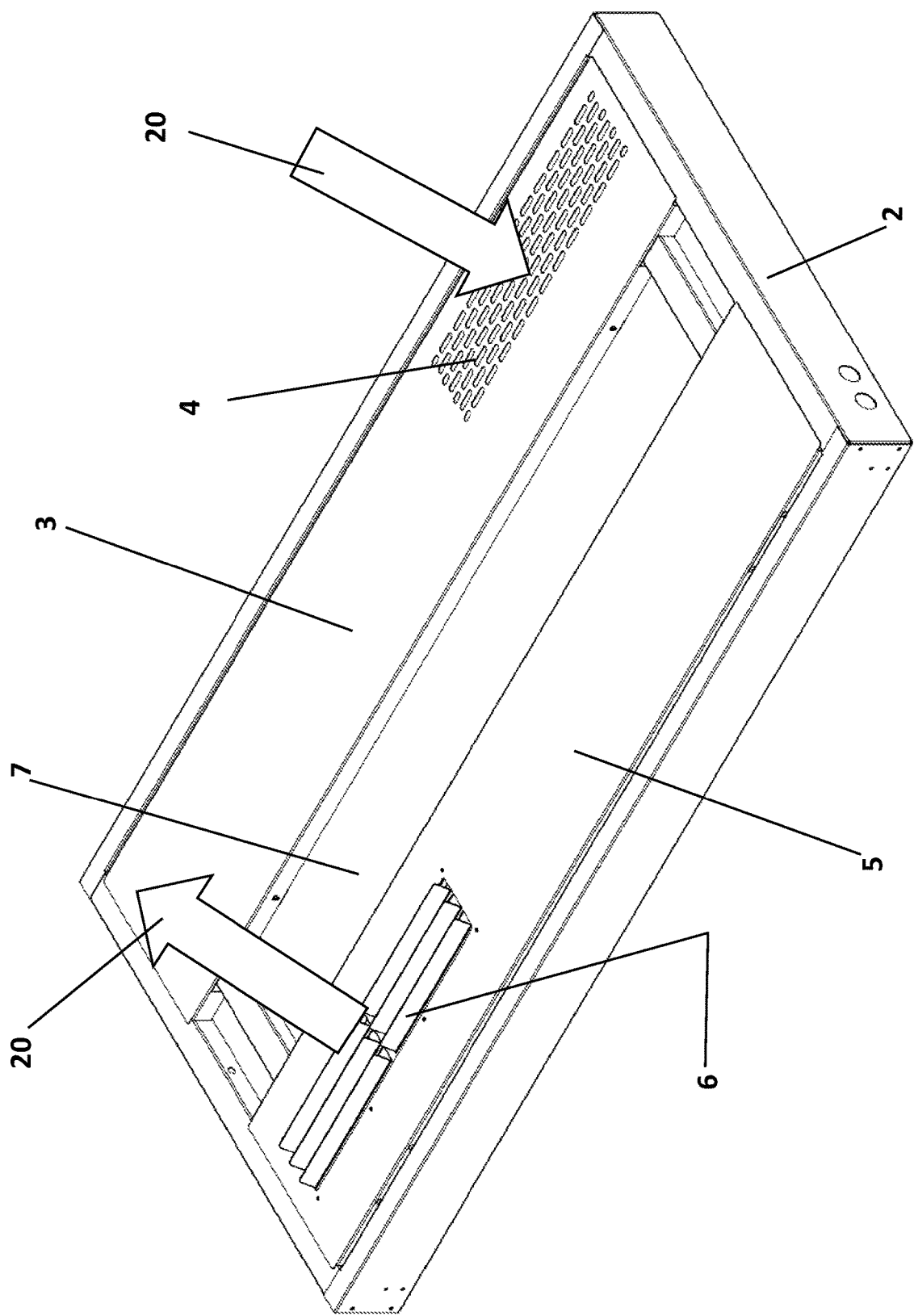
FIG. 1 is a bottom perspective view of the multi-channeled air purification device of the present invention.

The present invention is directed to an air purification device (designed to damage pathogens such as viruses and bacteria in the upper room air), it contains an air circulation apparatus to pull room air into the fixture, including the pathogenic micro-organisms contained therein, send the airstream through a configuration of multiple adjacent channels linked together in either a series or parallel fashion, each containing multiple ultraviolet light emitting diodes (LEDs) in specific wavelengths of 260 nm to 280 nm, cleansing the airstream and sending the airstream back into room.

The present invention is designed to optimize the elimination of airborne pathogens using ultraviolet light, by containing the wavelength of ultraviolet light within the maximum germicidal range of 260 nm-280 nm, maximizing the intensity by increasing the irradiance of the ultraviolet light source, limiting the distance to increase the proximity of the airborne pathogens to the ultraviolet source and increasing the duration of exposure.

With the development of light emitting diodes (LEDs), it is now possible to produce precise ultraviolet wavelength and intensity. The UV region covers the wavelength range 100-400 nm and is divided into three bands: UVA (315-400 nm) UVB (280-315 nm) UVC (100-280 nm). The Ultraviolet C band (UVC or UV-C) is ultraviolet radiation that is most effective for pathogen eradication. In nature, UV radiation from the sun is filtered out by the ozone layer so that it allows some UVA exposure, UVB has less exposure, and with UVC only a minimum amount reaches the earth's surface. The present invention uses LEDs emitting the precise wavelengths of 265 nm and/or 275 nm to isolate the ultraviolet spectrum within the maximum germicidal effective range. In addition, due to the precise wavelength control, the UV spectrum does not reach below 240 nm; therefore, no harmful ozone is produced by the fixture.

The present invention is designed with interconnected exposure chambers, these chambers are in series, or parallel, where chambers containing the LED modules, referred to herein as light channels, are positioned inside the device. Air is pulled into the fixture from the base of one side and routed through the fixture, it is sent either in parallel or back and forth in series through light channels, to be exhausted at the opposite end of the fixture. This can effectively change or extend the distance of travel through the light channels of the fixture by 100-500%, or X-% depending on the number of light channels (X), thereby extending the duration of exposure. The length of airstream exposure is directly related to the total dosage of UVC light in $mJ/cm^2$.

The back-and-forth motion of the air flow through the chambers causes turbulence. This slows the airspeed and causes the air, and the pathogens contained within, to "tumble" within the fixture. This further extends the duration of exposure of the micro-organisms to the ultraviolet light. Lastly, the turbulence of the air movement within the light channels also exposes the pathogens to ultraviolet light from multiple angles as they pass through the device, as well as providing high chances of "closed circuit" conditions—that is, second, third and more exposure opportunities. In comparison to a straight-line airflow, this back-and-forth flow greatly increases the exposure and decreases the "shadow effect" of one micro-organism coming between the light source and another micro-organism. The design of the chambers of the invention and the orientation of the LED modules within the chambers keep the airflow and pathogens within a maximum acceptable distance from the ultraviolet light sources.

The LED industry is advancing the technology at a very rapid pace. With recent advancements in the efficacy (light output per watt) of light emitting diodes, it is now possible to increase the irradiance of ultraviolet LED chips to levels not possible only a few years ago. The invention uses advanced LED chips and precise circuit board design layout to increase the irradiance within the fixture to extremely high levels, yet fully containing the UV light inside the fixture light channels to keep the device safe for use around people.

The exact nanometer wavelengths used covers the germicidal vulnerability spectrum. The solid-state LED technology employed allows the system to deliver precise wavelength dosages and an onboard microprocessor allows for any precise intensity configuration. The LED technology has instant-on capabilities that do not require long warmup periods like earlier fluorescent and induction technologies. The LED technology runs more efficiently when airflow cools it as opposed to fluorescent mercury tube light technology which has UV output loss when cooled. The LED UV-C component of the device is modular and can be replaced with any nanometer wavelength required to eradicate pathogens known today or discovered in the future. The dosage is a combination of wavelength, intensity, and duration.

An air circulation (cubic feet per minute (CFM)) helps to clean room or area air many times per hour. The fan unit is controllable and is also modular in design where fan-packs can be replaced or upgraded to tackle situations where distance or filtration may impede the flow of air through the device.

One embodiment of the present invention is sized at 2'×4', which is a standard commercial lighting fixture size, so it fits into any commercial ceiling grid configuration. Other variations include sizes of 5"×48" slimline architectural unit as well as 2'×2' drop in ceiling grid model. The exact dimensions are not critical and can be custom sized to fit many sized openings. The present fixture utilizes a modular fan, modular LED engine, controlled exposure chamber, alternating or parallel exposure chambers, accompanied by controls to further expand the usage and controllability of a fixture dosage, or any combination of the above listed, This provides an easy installation compatible with all standard 120-277 VAC electrical systems. The replaceable LED modules allow for years of reliable service with the same fixture and easy upgrade. The filters are easily changed or cleaned for long lifespan. In addition, the fixture is not limited to commercial ceiling grid configuration. It can also be surface, pendent, or chain mounted, or configured in a "linking" fashion where multiple fixtures are linked together or near each other to provide an architectural look as well as synergistic effect in air purification.

Using microprocessors and remote controls, the system can be set to specific configurations for dosage intensity, delivery time, room circulation or to conserve UV-C LED diode lifespan. The system can be customer-configured for any dosage requirements required today or in the future. Multiple fans can be used for enhanced airflow CFM and for pressure or airflow resistance.

Using occupancy sensors, the system can detect that people are present and turn on the UVC system. Then after the last room occupancy triggers a timeout, it can set the run time duration before shutdown. This can be set to run at a specific dosage for a specific time period, then reduce the dosage for another period and shut off after final no-occupancy period has elapsed.

The design of the present invention allows for easy installation into a standard commercial grid drop-ceiling structure found in most office, medical and school facilities. The invention is not limited to these uses and can be used in the home or vehicles, including mass transit trains, buses, ferries, ships, or planes for example. The unit accepts universal 120V-277 VAC electrical power input and the power supplies are modular to be replaced by 480 VAC power supplies where required. The system can also be power up with direct current (DC) electrical input using standard DC/DC converters. The LED modules are swappable and allow for easy onsite maintenance to be performed so that the fixture can have an extended lifespan or upgrades can be added. The filters are easily accessible for washing or replacement.

The present invention employs digital circuitry and recent advancements in wired and wireless technology that allow it to remotely acquire operational data and manipulate many digital functions from the control circuit board. The invention is equipped with sensory features, which can monitor the airflow conditions and UV-C efficiency of the fixture's operation which can be used to calculate the exact UV-C dose being delivered. The control features, which can adjust the intensity of the LEDs using 0-10V, pulse-width modulation (PWM) or resistance dimming and adjust the duration of exposure by controlling the fan speed, are used to set or change the device to a specific dosage delivery configuration. These control adjustments can be made through wired or wireless technology. Control scheduling can be used to automatically set operational time schedule of the device.

As can be seen in the figures, the multi-channeled air purification device of the present invention is a rectangular box-like unit 2 having an air input 4 and an air output 6. The shape of the device is not critical and so it is not limited to a rectangular geometry. It is discussed as a box-like shape for purpose of understanding and so other shapes are also contemplated. Further, the bottom and sides for the device have not been illustrated in every figure so that the interior can be illustrated, due to these sides being blank surfaces with no features pertaining to the importance of comprehending the function of the invention. The top of the fixture shown in FIG. 1 is composed of a fixture body 2, an air intake access panel 3, an air intake 4 that allows air 20 to enter the fixture, a fan access panel 5, an airflow output 6 that allows air flow 20 out of the fixture into the environment, and a LED module panel 7 that houses the LED boards internally away from exterior exposure to the elements and strictly kept contained within the light channels. These cover materials are usually metal but could be made out of a UVC-resistant plastic or plexiglass. Because the LED boards give off heat, they benefit from the LED module door being made out of metal, causing it to act as one large heat sink. Also, means for attaching the cover to the device is not shown, as well as the means to attach the device to a ceiling, but conventional attachment can be done using conventional attachment means such as screws, hooks and the like.

Figure 2:
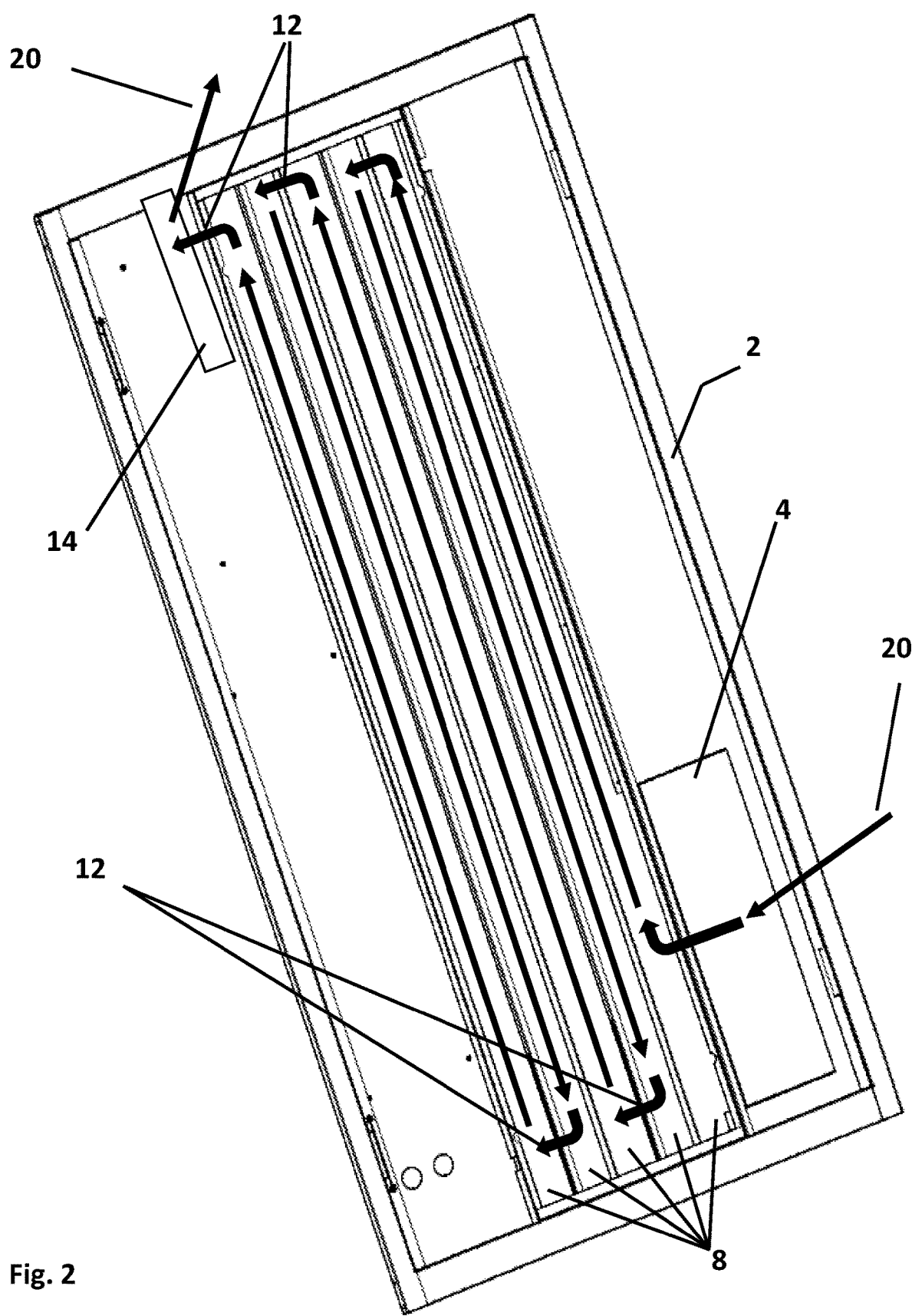
FIG. 2 is a top perspective view of the multi-channeled, series-configured, air purification device of the present invention.
Figure 3:
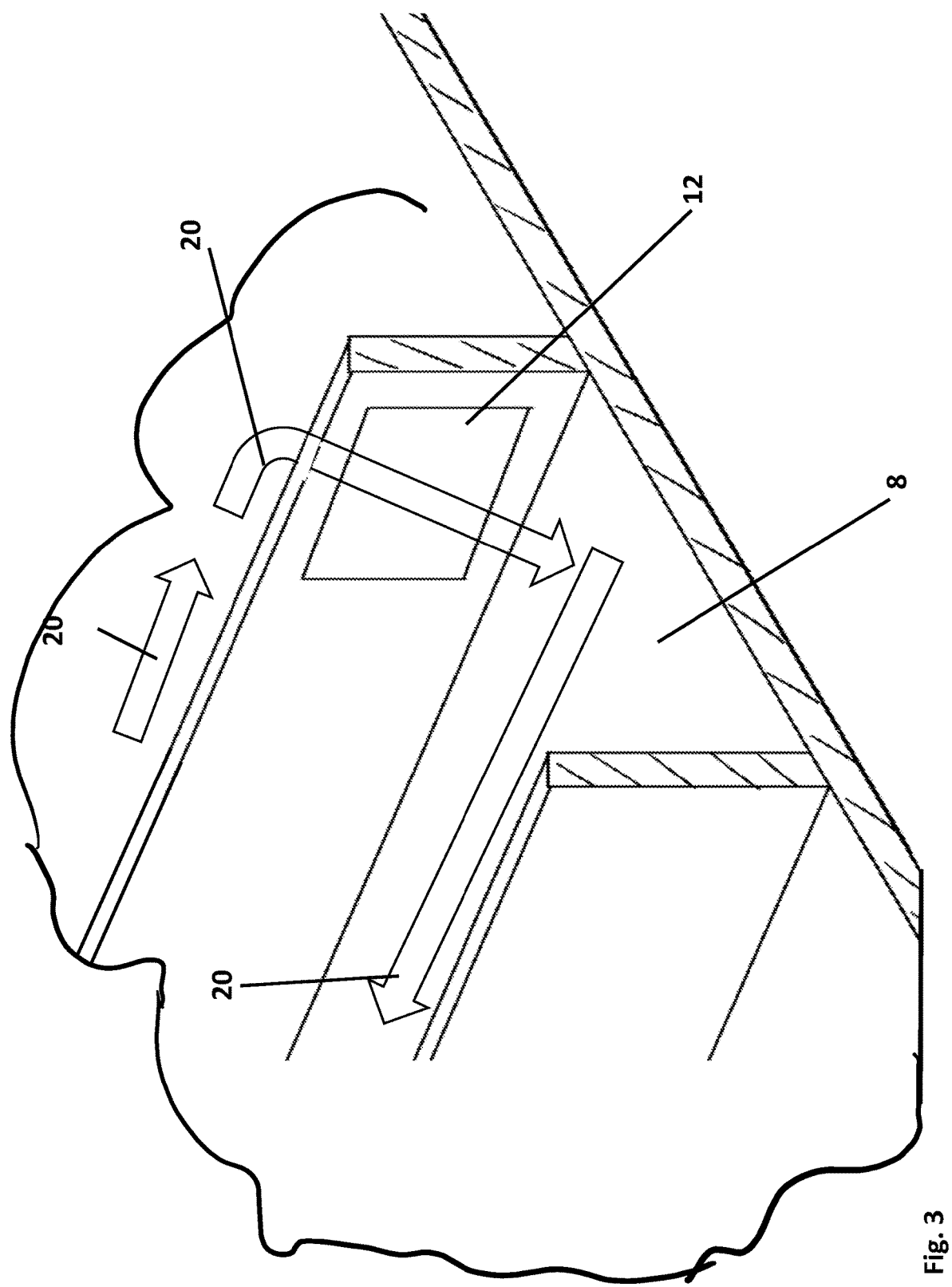
FIG. 3 is a cross sectional side view of the channels.
Figure 4:
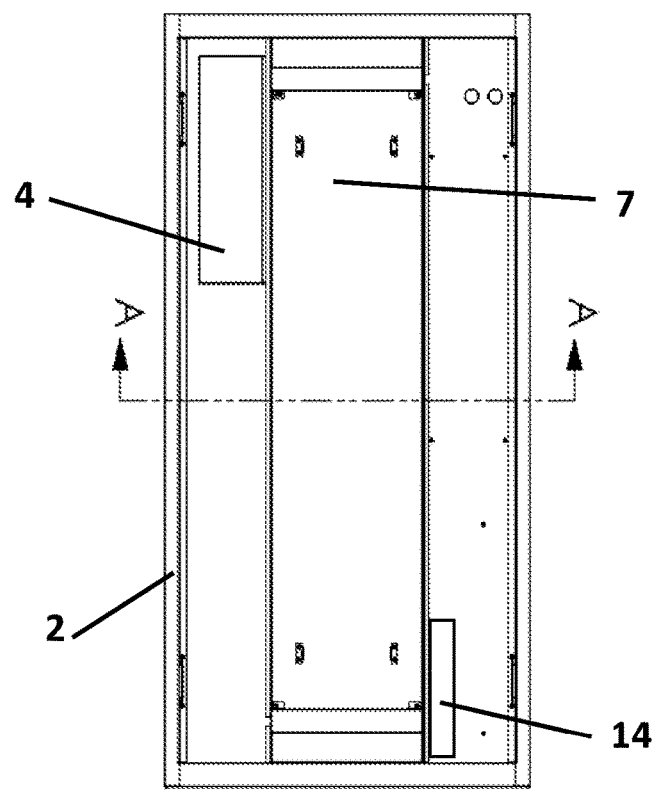
FIG. 4 is a top view of the present invention.
Figure 4A:
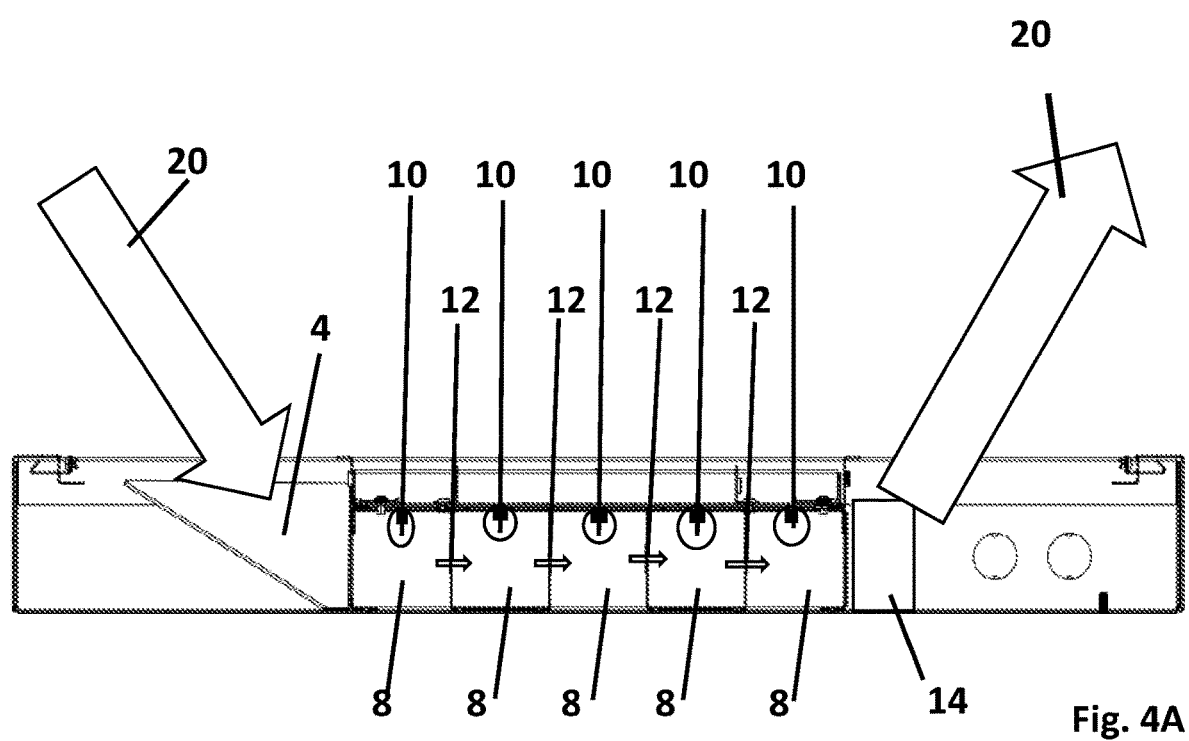
FIG. 4A is a cross-sectional view of the device of FIG. 4 taken along line A-A.

FIGS. 4 and 4A show an overhead and cross-sectional view, respectively, of how the air input flows into a plurality of parallel UV-C light channels 8 linked in series, each of which is a linear flow channel having a UV-C light source 10 along at least one surface/wall of each channel. A transition opening 12 (See also, FIG. 3) is provided in each channel to allow the air 20 to move from one channel to the adjacent channel. This allows the air 20 to travel in a "snake-like" back and forth pattern (See FIG. 2) while being exposed to the UV-C light. In the embodiment(s) shown in FIGS. 1-4A, a series configuration is depicted. The air 20 then exits from the device via the air outlet 6. A fan 14 facilitates the transit of the air by pulling air into the device and pushing the air 20 out. The fan can be of any known air-moving means; axial, blower, cross flow, etc.

Figure 5:
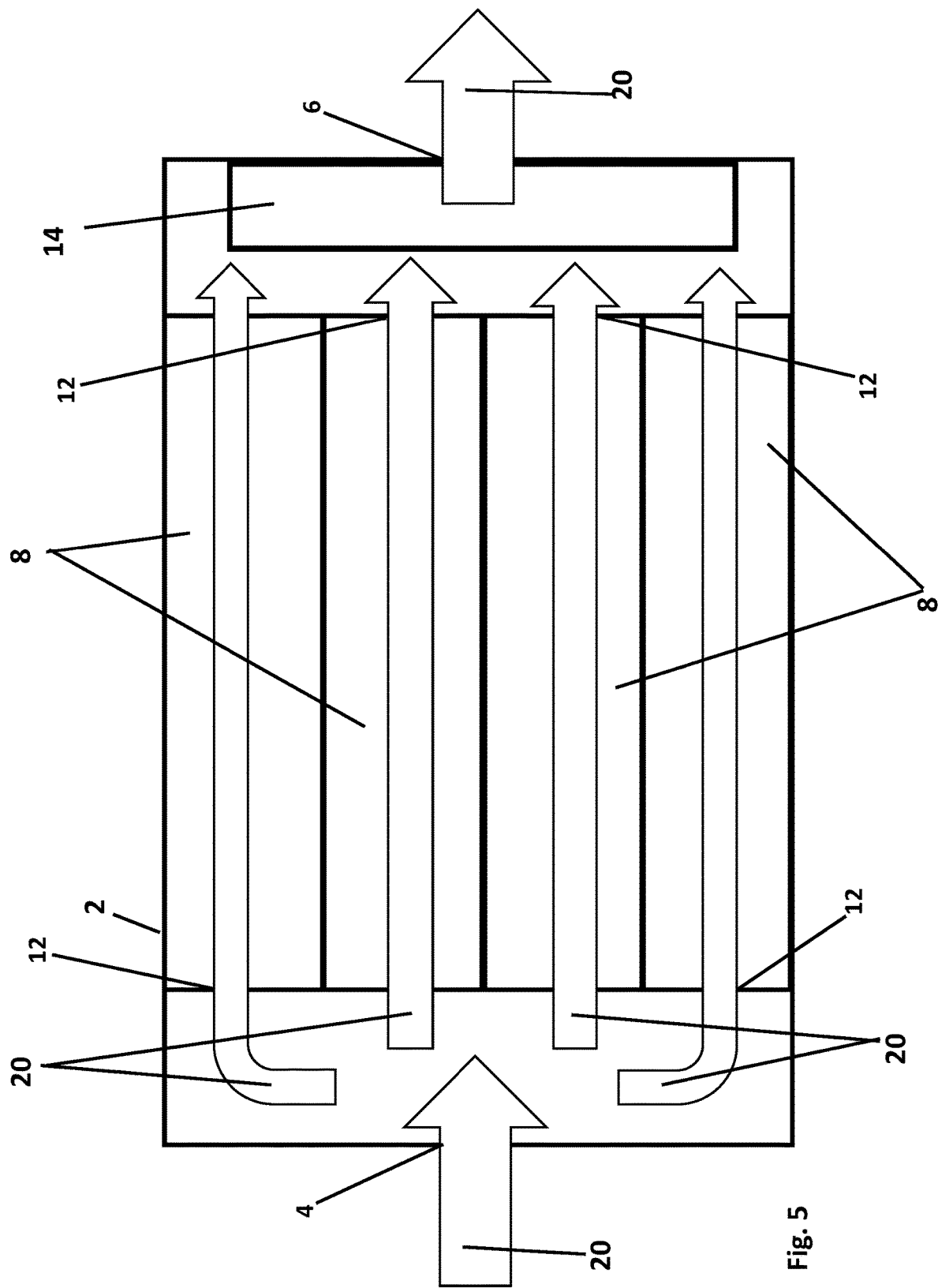
FIG. 5 is an alternate embodiment of the present invention showing parallel air flow.

FIG. 5 shows a simplified embodiment of UV-C light channels linked for parallel air flow. An air intake 4 allows air to be drawn in due to the fan 14, located towards the air outlet 6. Once the air 20 enters the fixture 2, the air 20 is divided amongst a plurality of parallel UV-C light channels 8 that directs the airflow into the maximum accepted distance from the ultraviolet light source. 4 light channels 8 are depicted in this figure, but more or fewer can be used.

Figure 6:
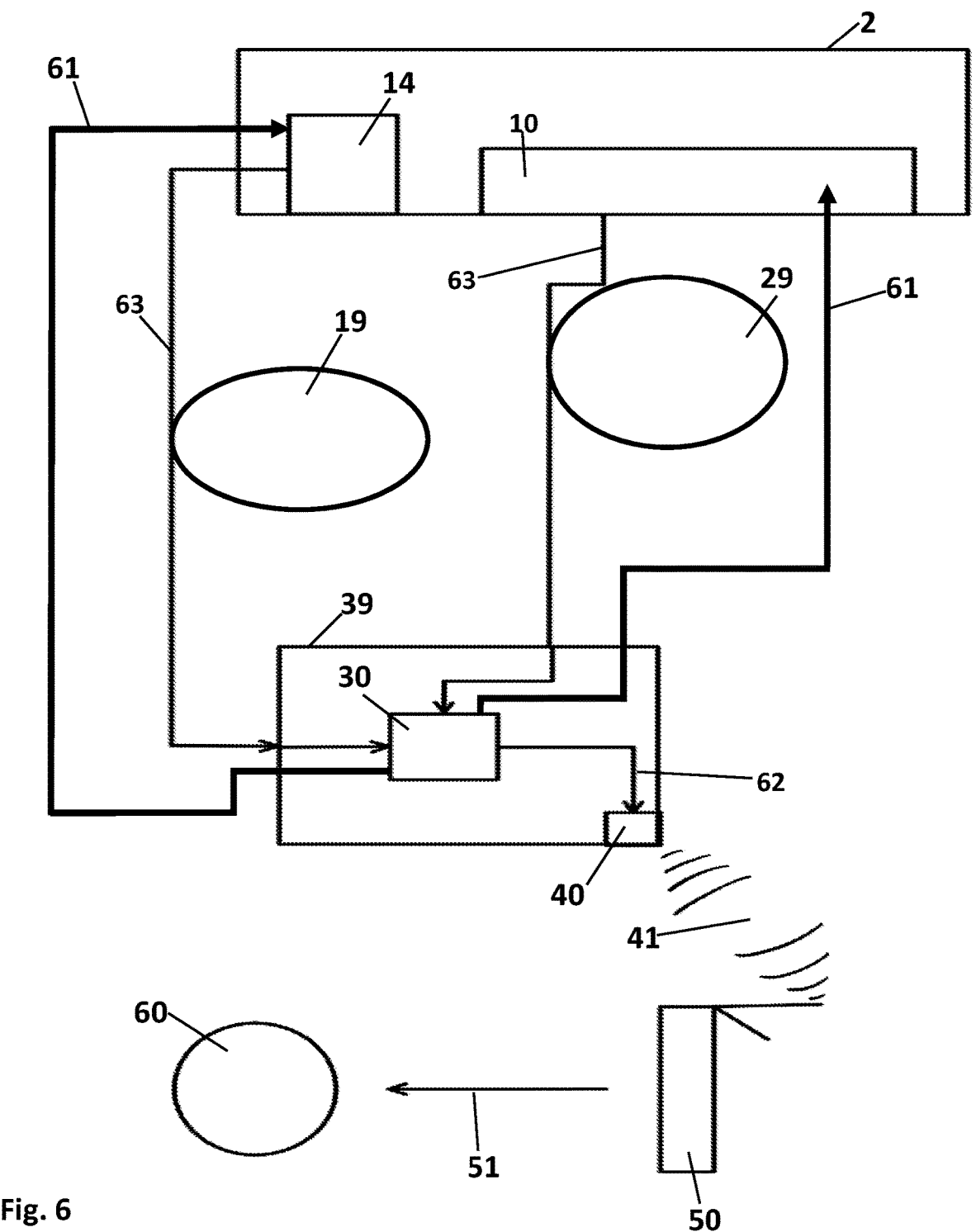
FIG. 6 is a circuit diagram of the present invention.

In an alternate embodiment of the present invention, it employs microprocessor-controlled equipment monitoring for airflow and dosage control, as well as solid-state LED technology to deliver precise UV-C reliability. See FIG. 6. The microprocessor 30 controls and adjusts the airflow through the device to provide exact duration component of the dosage. Airflow and dosage control are controlled by sending commands via wired or wireless (2.4 GHz, 9 MHz, or cellular) radio frequencies 41 to a circuit board 39 that includes a potential radio (if required) which controls a programmable fan 14 and the intensity of UVC LED module 10 via a control communication line 61. The airflow is monitored via a tachometer on the fan, or other air flow measuring means 19. The UV intensity is measured via voltage to the LEDs or with an ultraviolet light sensor 29 and sent to the processor 30 via a raw recorded data input line 63. With the controllability of these two factors, the device is able to deliver higher or lower doses on demand depending on each possible situation for a variation on scenarios.

Once the processor 30 outputs processed data 62 and transmits said data via a wired and or wireless antenna 40 means, the transmitted signal 41 is received by a gateway 50 that is checking for communication from the fixture at a predetermined interval of time. Each time communication is received from the wireless antenna 40 to the gateway 50, the received data is then sent to a cloud database 60 via cellular and or internet connection 51. This process allows for a lifetime run hours of LED boards and fan to be recorded and stored for maintenance purposes and send an alert as to when a predetermined lifespan has been met. Pairing this process with external sensors such as motion sensing/occupancy sensors, the fixture is able to purify the air only when necessary or desired and expand the overall life expectancy of the LED boards as well as the fan, allowing for the delivery of high variance of customization and controls to fit many scenarios.

The foregoing embodiments of the present invention have been presented for the purposes of illustration and description. These descriptions and embodiments are not intended to be exhaustive or to limit the invention to the precise form disclosed, and obviously many modifications and variations are possible in light of the above disclosure. The embodiments were chosen and described in order to best explain the principle of the invention and its practical applications to thereby enable others skilled in the art to best utilize the invention in its various embodiments and with various modifications as are suited to the particular use contemplated.

What we claim is:

1. A multichannel air purification device comprising
   a plurality of adjacent air channels in fluid communication with one another having a UV-C light source illuminate at least one air flow chamber,
   an air input means for allowing air into the channels, an air output means for allowing the air to exit the channels, openings between said channels for allowing air to pass from one channel to another channel, and a fan for drawing air through the device;
   communications controls for controlling an amount of UV-C light dosage administered by varying the speed of the fan as well as varying the intensity of UVC light sources wherein said communication controls are selected from wired communication and wireless communication;
   a cloud storage based database;
   a series of sensors that measure and record to the cloud storage based database air flow velocity and UVC intensity as sensed data,
   a gateway configured to initiate a log of the sensed data, at a predetermined time interval by communicating said sensed data to a cellular antenna or wired connection through said communication controls,
   wherein said communication controls is in communication with the cloud storage based database, for storing the sensed data, and
   wherein said cloud storage based service is configured for storing and monitoring the sensed data thereby enabling real time tracking of device energy consumption, device performance, and device lifespan.

2. The air purification device of claim 1 wherein said air channels have side walls and first and second ends, and said openings between said channels are located at the ends in opposite walls where channels are linked in series.

3. The air purification device of claim 1 wherein said channels have side walls and symmetric ends, and said openings between said channels are located at both ends of said channels, in which said openings allow for air to travel simultaneously through a plurality of channels in a parallel fashion.

4. The air purifier of claim 1, wherein said wireless communication is via a radio frequency controller and is selected from 2.4 GHz, 900 MHz, and cellular.

5. The air purification device of claim 1 wherein said air flow is calculated from readings from a tachometer that measures RPMs of a fan, and wherein said UVC intensity measurement is selected from a direct UVC sensor, a voltage meter, an ammeter, and combinations thereof, and output data is presented in units for airflow as feet per second, and UVC intensity as microwatts per square centimeter.

\* \* \* \* \*